United States Patent [19]
Kordecki

[11] Patent Number: 5,977,782
[45] Date of Patent: Nov. 2, 1999

[54] FLUID ABRASION AND/OR CORROSION SENSORS AND METHOD OF SENSING ABRASION AND/OR CORROSION

[75] Inventor: David L. Kordecki, Elkhart, Ind.

[73] Assignee: CTS Corporation, Elkhart, Ind.

[21] Appl. No.: 09/012,851

[22] Filed: Jan. 23, 1998

[51] Int. Cl.$^6$ .................................................. G01R 27/02
[52] U.S. Cl. .......................... 324/700; 324/721; 340/631
[58] Field of Search ..................................... 324/700, 721; 340/631

[56] References Cited

U.S. PATENT DOCUMENTS

| | | |
|---|---|---|
| 3,108,242 | 10/1963 | Scott . |
| 3,124,771 | 3/1964 | Rohrback . |
| 3,609,549 | 9/1971 | Hausler et al. . |
| 3,854,087 | 12/1974 | Frenck et al. . |
| 3,857,094 | 12/1974 | Caldecourt . |
| 3,996,124 | 12/1976 | Eaton et al. . |
| 4,030,028 | 6/1977 | Allender . |
| 4,209,376 | 6/1980 | Arita et al. . |
| 4,214,951 | 7/1980 | Bernhardsson et al. . |
| 4,217,544 | 8/1980 | Schmidt . |
| 4,305,278 | 12/1981 | Stewart et al. . |
| 4,322,680 | 3/1982 | Janata et al. . |
| 4,326,164 | 4/1982 | Victor . |
| 4,337,668 | 7/1982 | Zupanick . |
| 4,338,563 | 7/1982 | Rhoades et al. . |
| 4,598,280 | 7/1986 | Bradford . |
| 4,666,582 | 5/1987 | Blankenship et al. . |
| 4,677,373 | 6/1987 | Kobayashi et al. . |
| 4,741,204 | 5/1988 | Luck et al. . |
| 4,752,360 | 6/1988 | Jasinski . |
| 4,755,744 | 7/1988 | Moore ..................................... 324/700 |
| 4,780,664 | 10/1988 | Ansuini et al. . |
| 4,827,242 | 5/1989 | Blankenship et al. . |
| 4,839,580 | 6/1989 | Moore ..................................... 324/700 |
| 4,863,572 | 9/1989 | Jasinski . |
| 4,994,159 | 2/1991 | Agarwala et al. . |
| 5,211,677 | 5/1993 | Sargeant et al. . |
| 5,243,297 | 9/1993 | Perkins et al. . |
| 5,269,175 | 12/1993 | Chmiel et al. . |
| 5,286,357 | 2/1994 | Smart et al. . |
| 5,306,414 | 4/1994 | Glass et al. . |
| 5,310,470 | 5/1994 | Agarwala et al. . |
| 5,312,536 | 5/1994 | Pai et al. . |
| 5,332,961 | 7/1994 | Hammerle . |
| 5,338,432 | 8/1994 | Agarwala et al. . |
| 5,437,773 | 8/1995 | Glass et al. . |
| 5,457,396 | 10/1995 | Mori et al. . |
| 5,596,266 | 1/1997 | Mori et al. . |

*Primary Examiner*—Josi Ballato
*Assistant Examiner*—Jose M. Solis
*Attorney, Agent, or Firm*—Schmeiser, Olsen & Watts

[57] ABSTRACT

A sensor is provided with a conductive sensing element that has a composition adapted to provide a resistance large enough that predetermined magnitudes of voltage noise do not create a false indication of removal, e.g. by abrasion or corrosion. Also, the sensing element composition is adapted to provide a temperature coefficient of resistivity small enough that measurements are substantially independent of temperature. Resistance is preferably greater than 10 ohms and the absolute value of TCR is preferably less than 1000 parts per million per ° C. The conductive sensing element may be formed from several materials, including alloys of palladium or lead, particularly palladium-gold, lead-bismuth, or lead-palladium. A combination sensor is provided that includes an abrasion sensing element and a corrosion sensing element on the same substrate. A multi-purpose sensor with a single sensing element is provided by incorporating attributes of both an abrasion sensor and a corrosion sensor such that the multi-purpose sensor is susceptible both to abrasion and corrosion. A method is also provided for detecting when selected characteristics of a subject fluid, such as abrasiveness or corrosiveness, exceed a predetermined limit.

24 Claims, 2 Drawing Sheets

FLUID ABRASION AND/OR CORROSION SENSORS AND METHOD OF SENSING ABRASION AND/OR CORROSION

BACKGROUND OF THE INVENTION

1. Technical Field

This invention relates to the field of fluid sensors. More specifically the invention relates to fluid abrasion sensors, fluid corrosion sensors, combined abrasion and corrosion sensors, and a method for sensing abrasion and/or corrosion.

2. Background Art

Abrasion sensors and corrosion sensors are particularly important when an increase in the abrasiveness or corrosiveness of a fluid, such as oil, aqueous solution, or water, may damage equipment or upset a process. Some sensors exist that monitor the abrasiveness or corrosiveness of a fluid and yield a quantitative value such as milligrams of particulate matter per liter of fluid for abrasiveness or the pH for corrosiveness. Such sensors are typically expensive to purchase, use, and maintain and often may be used only in limited circumstances due to their fragility. Also, a quantitative value is often not needed so long as a sensor indicates when the abrasiveness or corrosiveness of a fluid exceeds an allowable limit. This is particularly true for internal combustion engines, hydraulic systems, and the like wherein abrasive particles and/or corrosive acids readily accumulate in oil circulating through such a device or system.

One type of sensor exists that includes a sacrificial amount of a conductive substance. The conductive substance is selected so that it will abrade or corrode when the respective abrasiveness or corrosiveness of the subject fluid exceeds an allowable limit. Also, the conductive substance is selected to corrode or abrade rapidly enough that the condition may be detected before significant damage to equipment or processes occur. Essentially, such a sensor will exhibit a given resistance (typically measured in ohms) when newly exposed to the subject fluid, but the resistance will increase as the conductive substance wears away, typically by abrasion or corrosion. Most commonly, such sensors are connected to electronic circuitry capable of measuring the resistance of the sensor. The electronic circuitry is used to apply a voltage across the sensor and measure the resulting current. The equation $R=V/i$, wherein R is resistance, V is voltage and i is current, can then be used to calculate the measured resistance. For abrasion sensors, such devices are described in U.S. Pat. No. 4,305,278 to Stewart et al., U.S. Pat. No. 4,337,668 to Zupanick, and U.S. Pat. No. 5,211,677 to Sargeant et al., each of which is hereby incorporated by reference for their pertinent and supportive teachings. For corrosion sensors, such devices are described in U.S. Pat. No. 3,108,242 to Scott, Jr., U.S. Pat. No. 3,124,771 to Rohrback, U.S. Pat. No. 3,854,087 to Frenck et al., U.S. Pat. No. 3,857,094 to Caldecourt, U.S. Pat. No. 4,217,544 to Schmidt, U.S. Pat. No. 4,326,164 to Victor, U.S. Pat. No. 4,338,563 to Rhoades et al., U.S. Pat. No. 4,741,204 to Luck et al., U.S. Pat. No. 4,780,664 to Ansuini et al., U.S. Pat. No. 5,243,297 to Perkins et al., and U.S. Pat. No. 5,332,961 to Hammerle, each of which is hereby incorporated by reference for their pertinent and supportive teachings.

Many types of fluids, for example, lubricating oil and hydraulic fluid, contain additives to prevent the buildup of corrosive compounds. Corrosion typically is limited if the fluid contains the proper amount and type of additives. The corrosive compounds are still generated, but the additives change the chemical characteristics of the corrosive compounds such that corrosion is suppressed. However, as the fluid ages, the additives are depleted and corrosive compounds begin to accumulate in the fluid. When a corrosion sensor of the type described above is present, the conductive substance will begin to corrode and the sensor's resistance will change, thus signaling an accumulation of corrosive compounds. Typically, an elemental metal such as lead or copper is selected for the conductive substance. It is a problem among the metals most often used that their resistivity is temperature dependent and a change in temperature of the fluid may be mistaken for an increase in corrosiveness. Accordingly, conventional corrosion sensors include a temperature reference for performing temperature correction of any changes in the measured resistance. Often, a Wheatstone bridge or Kelvin bridge arrangement is used as shown in several of the references indicated above. Unfortunately, requiring a temperature reference adds to the complexity and cost of a corrosion sensor and a sensor that does not require temperature correction is highly desirable.

It is also a problem among the metals most often used that their resistivity is relatively low, typically yielding corrosion sensors having a resistance of 1 ohm or less. It is a significant disadvantage of conventional corrosion sensors that their low resistance necessitates a relatively low applied voltage, allowing electrical noise to significantly influence measuring the resistance. This condition renders it difficult at times to reliably determine whether a change in resistance is from corrosion or just electrical noise. Accordingly, a sensor that reliably distinguishes between noise and corrosion is highly desirable.

Many types of equipment and processes that use fluids, for example, engines and hydraulic systems, include devices, for example, filters, to remove abrasive matter and prevent its buildup in the fluid. Abrasion typically is limited if the device works properly, however, the device may rupture or clog and allow abrasive matter to pass through it or around it via a bypass valve. When an abrasion sensor of the type described above is present, the conductive substance will begin to abrade and the sensor's resistance will change, thus signaling an accumulation of abrasive matter. Typically, an elemental metal or metal alloy such as nickel-chromium is selected for the conductive substance. It is a problem of many metals that their resistivity is temperature dependent as discussed above for corrosion sensors and a temperature reference is required. Unfortunately, requiring a temperature reference adds to the complexity and cost of an abrasion sensor too, so a sensor that does not require temperature correction is highly desirable. Also, as discussed above for corrosion sensors, it is a problem of conventional abrasion sensors that they have a resistance of 1 ohm or less. Accordingly, an abrasion sensor with a greater resistance to reliably distinguish between noise and abrasion is highly desirable.

Thus, it can be seen from the above discussion that it would be an improvement in the art to provide an abrasion sensor and a corrosion sensor that do not require temperature correction and reliably distinguish noise from abrasion or corrosion.

DISCLOSURE OF INVENTION

According to the present invention, a sensor is provided with a conductive sensing element, wherein a sensing voltage applied across the sensing element creates a sensing current used to determine an electrical resistance. The sensing element has dimensions and a composition adapted to indicate removal of a portion of the sensing element by an increase in the electrical resistance and to provide a resistance large enough that predetermined magnitudes of voltage noise do not influence the sensing current to create a false indication of removal. Also, the sensing element composition is adapted to provide a temperature coefficient of resistivity small enough that measurement of the increase in resistance is substantially independent of temperature. For example, resistance should be greater than 10 ohms and the absolute value of TCR should be less than 1000 parts per million per ° C. Also by way of example, the conductive sensing element may be formed using alloys of palladium or lead, particularly palladium-gold, lead-bismuth, or lead-palladium. The palladium-gold alloy is especially well-suited for abrasion sensors, while the lead-bismuth and lead-palladium alloys are especially well-suited for corrosion sensors. Exemplary sensors include those having a thin film deposition of the metal alloy on a substrate with a thin film of a chromium-containing substance between the alloy and substrate to promote adhesion.

A combination sensor is also provided, for example, by forming an abrasion sensing element and a corrosion sensing element on the same substrate. A multi-purpose sensor with a single sensing element is also provided, for example, by incorporating attributes of both an abrasion sensor and a corrosion sensor such that the multi-purpose sensor is susceptible both to abrasion and corrosion.

According to the present invention, a method is also provided for detecting when selected characteristics of a subject fluid, such as abrasiveness or corrosiveness, exceed a predetermined limit. The method includes the steps of exposing a sensor according to the present invention to a fluid and allowing the fluid to remove a portion of the sensing element, causing an increase in the electrical resistance. The removal will thus be reliably detected without temperature correction.

The foregoing and other features and advantages of the present invention will be apparent from the following more particular description of preferred embodiments of the invention, as illustrated in the accompanying drawings.

BRIEF DESCRIPTION OF DRAWINGS

Preferred embodiments of the present invention will hereinafter be described in conjunction with the appended drawings, where like designations denote like elements, and.

BEST MODE FOR CARRYING OUT THE INVENTION

According to a preferred embodiment of the present invention, a sensor is provided having an adequately large resistance and an adequately small temperature coefficient of resistivity (TCR) such that removal of its conductive sensing element may be reliably detected without temperature correction. Essentially, the sensing element is formed so that portions are removed when selected characteristics of a subject fluid, such as abrasiveness or corrosiveness, exceed a predetermined limit. Such a sensor will exhibit a given resistance (typically measured in ohms) when newly exposed to the subject fluid, but the resistance will increase as the conductive substance wears away, often by abrasion or corrosion. Through the change in resistance, exceeding a predetermined limit for a characteristic, such as abrasiveness or corrosiveness, may be detected. A method is also provided for detecting when selected characteristics of a subject fluid exceed a predetermined limit. The method includes the steps of exposing a sensor according to the present invention to a fluid and allowing the fluid to remove a portion of the sensing element, causing an increase in the electrical resistance.

The terms abrasion, abrade, abrasiveness, etc. as used herein refer to a process by which insoluble particles accumulate in a fluid and cause wear to equipment or upset a process. Such particles may result from dust, carbon, degradation products from the fluid, equipment wear debris, corrosion products, and the like. The terms corrosion, corrode, corrosiveness, etc. as used herein refer to a process by which chemical compounds accumulate in a fluid and cause wear to equipment or upset a process. Such compounds may result from depletion of anti-corrosion additives in a fluid or other mechanisms. Often, corrosive compounds are generated continuously, but the additives change the chemical characteristics of the corrosive compounds such that corrosion is suppressed. As the fluid ages, the additives are depleted and corrosive compounds begin to accumulate in the fluid.

Figure 1:
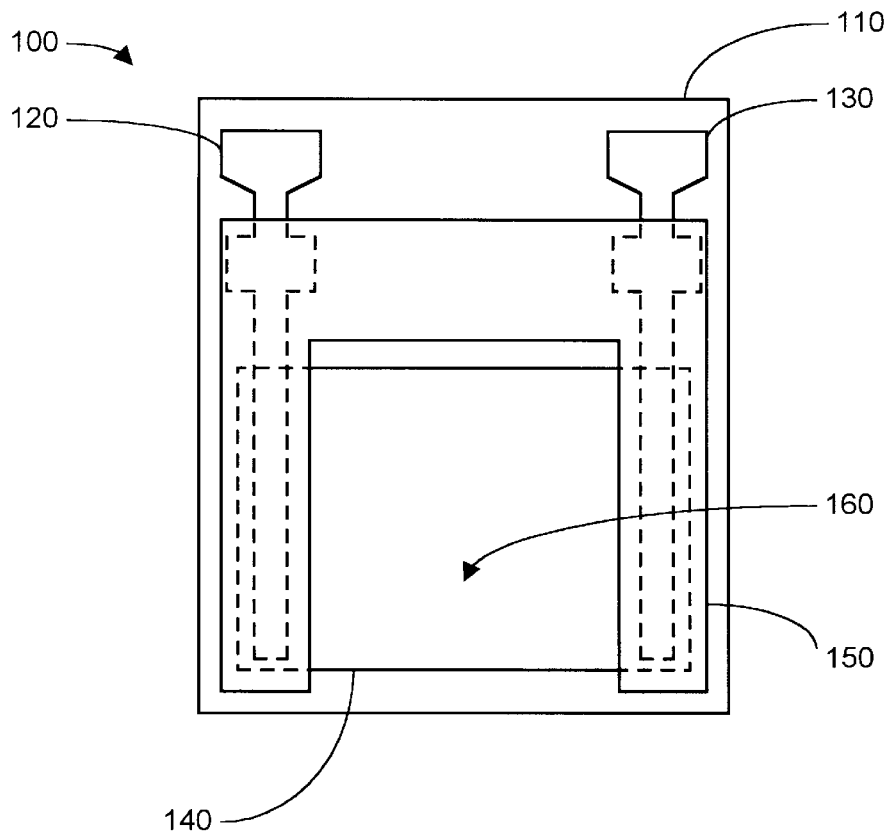
FIG. 1 is a view of an abrasion sensor of the present invention.

Referring to FIG. 1, an abrasion sensor 100 is shown. An exemplary abrasion sensor 100 includes a substrate 110, contact pads 120 and 130, and a conductor 140. The dimensions and positions of contact pads 120 and 130 and conductor 140 on substrate 110 as shown in FIG. 1 may be substantially altered without departing from the spirit and scope of the present invention. Any dimensions or positions known in the art that are consistent with the present invention are suitable. Several possible dimensions or positions are proposed in the patents listed and incorporated by reference above, most of which would be consistent with the present invention. One major difference, however, is that a temperature reference, Wheatstone bridge, Kelvin bridge, and the like are not required in a sensor according to the present invention.

Preferably, substrate 110 is substantially planar and made from electrically insulating material, that is, a material of relatively high resistance such as a ceramic, for example, alumina, glass, sapphire, or porcelain. Alternatively, substrate 110 could have a differently shaped surface as in the case of a dish-shaped sensor, cylindrical sensor, or column-shaped sensor with a triangular or rectangular cross-section. Nevertheless, the resistance should be high enough relative to conductor 140 such that any conduction through the substrate does not substantially influence measurement of the resistance of conductor 140. Other materials may be suitable as well for substrate 110 provided contact pads 120 and 130 and conductor 140 can adhere to the substrate. Substrate 110 is approximately square in shape and about 1.25 cm (0.5 in.) wide by 1.25 cm (0.5 in.) high or of a different shape with a similar area. Substrate 110 may also be sized smaller since it is not required to include a temperature reference on substrate 110.

Contact pads 120 and 130 are preferably a ceramic-metal (cermet), such as silver cermet, or another substance suitable for forming solder connections to conductor 140. Contact pads 120 and 130 may be deposited on substrate 110 by a thick film process, such as screen printing, or another process also suitable for forming solder connections to conductor 140.

Conductor 140 is preferably a thin film deposition of a conductive substance on substrate 110 with a thin film of a chromium-containing substance between conductor 140 and substrate 110 to promote adhesion. As used herein, the term "thin film" refers to a layer of material deposited by a thin film deposition technique such as vapor deposition, vacuum evaporation, vacuum sublimation, sputtering, and other methods known in the art. Alternatively, conductor 140 could be a thick film deposition of a conductive substance, a metal foil, or the like, though they are not preferred. Conventionally, a ceramic material is used for substrate 110 and it must be ground to improve the surface finish before applying conductor 140, however, no such limitation exists in the present invention. Accordingly, an unground ceramic material for substrate 100 is acceptable. Conductor 140 forms an electrical connection with contact pads 120 and 130 such that contact pads 120 and 130 may be connected to electronic circuitry (not shown) capable of measuring the resistance of abrasion sensor 100. Typically, the electronic circuitry is used to apply a voltage across abrasion sensor 100 and measure the resulting current. The equation $R=V/i$, wherein R is resistance, V is voltage and i is current, can then be used to calculate the measured resistance. Caution must be exercised in apply the voltage across abrasion sensor 100, otherwise, excessive current may damage it. This is especially true where conductor 140 is a thin film that is easily damaged by excessive current.

Notably, the equation above can be rearranged to $V_{max}=i_{max}R$, wherein $i_{max}$ is the maximum current that sensor 100 may tolerate and $V_{max}$ is the corresponding maximum voltage that may be applied for a given resistance. Accordingly, if sensor 100 is designed to provide a higher resistance, then the maximum voltage that may be applied across abrasion sensor 100 will increase even though $i_{max}$ remains unchanged. Conventional abrasion sensors typically have a resistance of 1 ohm or less but, for abrasion sensor 100, resistance is preferably greater than 10 ohms and most preferably greater than 100 ohms. Thus, a higher voltage may be applied across abrasion sensor 100 as compared to conventional sensors. It is a significant disadvantage of conventional sensors that their low resistance necessitates a relatively low applied voltage, allowing electrical noise voltages to significantly influence measuring the resistance. This condition renders it difficult at times to reliably determine whether a change in measured resistance is from abrasion or just electrical noise. Typically, attempts must be made to shield sensor 100 from noise or to use electronic controls to reduce it, however, such shielding and controls are costly and might not be reliable. Accordingly, abrasion sensor 100 possessing a higher resistance, for example, greater than 10 ohms, reduces cost and improves the reliability with which abrasion sensor 100 distinguishes between noise and corrosion.

Similarly, the TCR of conductor 140 should be between −1000 and +1000 parts per million per ° C., that is, the TCR absolute value should be less than 1000. In conventional abrasion sensors, a conductive substance is often selected with a TCR greater than 1000 parts per million per ° C. In other words, the resistivity is temperature dependent and a temperature reference, e.g., a Wheatstone bridge, Kelvin bridge or the like, is required. Without the reference or bridge, a change in temperature of the fluid may be mistaken for an increase in abrasiveness. Unfortunately, requiring a temperature reference adds to the complexity and cost of an abrasion sensor. Accordingly, there are significant advantages to an abrasion sensor that does not require a temperature reference, including the advantage of decreased size as mentioned above.

In the present invention, metals or metal alloys are suitable choices for conductor 140, although it is conceivable that other substances may be used, provided they comply with the criteria set forth herein for conductor 140. Metal alloys are preferred for conductor 140 since several alloy combinations and compositions exist that will meet the criteria for conductor 140 set forth herein. Also, a manufacturer may search among the several alloys of the present invention to select one that meets any custom criteria that must be satisfied for a particular abrasion sensor 100. For example, two custom criteria are the hardness and thickness of conductor 140. Both are heavily dependent on the particular circumstances of the application in which abrasion sensor 100 will be used. In general, the thickness is preferably 3000 nanometers (nm) or less, such as in one example where conductor 140 was 200 nm thick. The hardness of conductor 140 should be considered when selecting a thickness, since softer metal alloys tend to abrade more quickly and easily than harder ones. In some circumstances, it may be desirable for conductor 140 to abrade rapidly and quickly indicate an increase in abrasiveness. However, in other circumstances, an overly soft alloy may abrade too readily and give a false indication before the fluid actually reaches a predetermined abrasiveness limit.

Conductor 140 is most preferably a bimetallic alloy, particularly bimetallic alloys of 1% to 99% palladium or bimetallic alloys of 1% to 99% lead. A palladium-gold alloy of 5% to 95% palladium and a complementary amount of gold is especially well-suited for abrasion sensors. As discussed above, the composition of the palladium-gold alloy, or other bimetallic alloy, may be adjusted to meet the custom criteria of a particular abrasion sensor 100. For instance, an exemplary abrasion sensor 100 preferably includes a 50%±10% palladium/50%±10% gold alloy for its conductor 140. Such a bimetallic alloy will generally possess the highest resistivity and lowest TCR that can be obtained for the given alloy. If the amount of one metal in such an alloy is increased, then the alloy resistivity will decrease and approach the elemental metal resistivity, since the one metal will typically have a lower resistivity in its elemental state. Similarly, the alloy TCR will increase and approach the elemental metal TCR, since the one metal will typically have a higher TCR in its elemental state. Accordingly, the metals of a bimetallic alloy may be selected and the composition adjusted to achieve a desired resistivity and TCR. As indicated above, such selections and adjustments may also determine the acceptability of the alloy as to custom criteria, for example, hardness. Furthermore, the spirit and scope of the present invention also includes alloys of more than two metals, however, they are not preferred since it is more simple and cost effective to design and fabricate alloys of only two metal components.

As indicated in FIG. 1, abrasion sensor 100 may optionally be partially coated with a polymer 150 or other protective substance to prevent damage to contact pads 120 and 130 and their junctions with conductor 140. Abrasion of contact pads 120 and 130 or their junctions with conductor 140 potentially may yield erroneous readings from abrasion sensor 100. Applying polymer coating 150 is a simple, inexpensive method for preventing such a possibility. Any such polymers or substances known in the art are acceptable. For example, as indicated in FIG. 1, conductor 140 is arranged on substrate 110 with polymer coating 150 to form a sensing element 160. Sensing element 160, as shown, is one example of a pattern that provides a fluid target, that is, a pattern with a relatively large, continuous area of conductive substance suitable for impinging a fluid stream thereon. Sensing element 160 preferably provides such a fluid target so that a fluid stream can be easily directed toward sensing element 160 to contact it in a manner allowing particles in the fluid to abrade sensing element 160 and indicate an undesirable accumulation of particles in the fluid. The dimensions and position for sensing element 160 on substrate 110 as shown in FIG. 1 may be substantially altered without departing from the spirit and scope of the present invention. Any dimensions or positions known in the art that are consistent with the present invention are suitable. Several possible dimensions or positions are proposed in the patents listed and incorporated by reference above, most of which would be consistent with the present invention.

Figure 2:
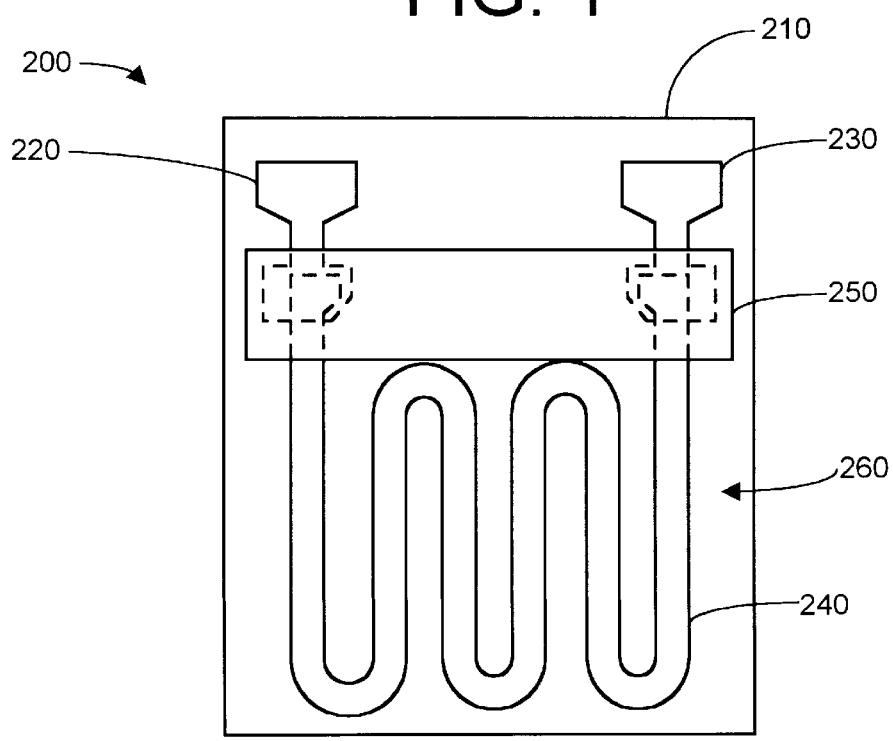
FIG. 2 is a view of a corrosion sensor of the present invention.

Referring now to FIG. 2, a corrosion sensor 200 is shown. In large part, the discussion above for abrasion sensor 100 also applies to corrosion sensor 200, but some differences exist. An exemplary corrosion sensor 200 includes a substrate 210, contact pads 220 and 230, and a conductor 240. As indicated above for abrasion sensor 100, the configuration of corrosion sensor 200 shown in FIG. 2 may be substantially altered without departing from the spirit and scope of the present invention. Also, the criteria discussed above for substrate 110 and contact pads 120 and 130 is equally applicable to substrate 210 and contact pads 220 and 230.

The discussion above for conductor 140, its arrangement, resistance, TCR, etc. is also equally applicable to conductor 240 except as to the selection of specific metals. A manufacturer may search among the several alloys of the present invention to select one that meets any custom criteria that must be satisfied for a particular corrosion sensor 200. For example, two custom criteria are the corrosion resistance and thickness of conductor 240. Both are heavily dependent on the particular circumstances of the application in which corrosion sensor 200 will be used. In general, the thickness is preferably 3000 nanometers (nm) or less, such as in one example where conductor 240 was 2,500 nm thick. The corrosion resistance of conductor 240 should be considered when selecting a thickness, since less resistant metal alloys tend to corrode more quickly and easily than more resistant ones. In some circumstances, it may be desirable for conductor 240 to corrode rapidly and quickly to indicate an increase in corrosiveness. However, in other circumstances, an easily corroded alloy may corrode too readily and give a false positive before the fluid actually reaches a predetermined corrosiveness limit.

Conductor 240 is most preferably a bimetallic alloy, particularly alloys of 1% to 99% palladium or 1% to 99% lead. A lead-palladium or lead-bismuth alloy of 5% to 95% lead and a complementary amount of palladium or bismuth is especially well-suited for corrosion sensors. As discussed above, the composition of the bimetallic alloy, may be adjusted to meet the custom criteria of a particular corrosion sensor 200. For instance, an exemplary corrosion sensor 200 preferably includes a 50%±10% lead/50%±10% bismuth or palladium alloy for its conductor 240. Such a bimetallic alloy will generally possess the highest resistivity and lowest TCR that can be obtained for the given alloy. The discussion above for adjusting the composition of conductor 140 to achieve a certain resistivity, TCR, or custom criteria and the discussion for polymer coating 150 is equally applicable to conductor 240 and polymer coating 250.

As indicated in FIG. 2, conductor 240 is arranged on substrate 210 to form a sensing element 260. Sensing element 260 as shown is one example of a serpentine-shaped pattern suitable for increasing the resistance of conductor 240. The serpentine pattern is used to keep resistance high since the cross-sectional area at any given point along a conductor is relatively small and the length is relatively large. Accordingly, a small cross-sectional area and long length for conductor 240 according to the present invention help to boost resistance higher than the target-shaped pattern discussed above would provide. The dimensions and position of sensing element 260 on substrate 210 as shown in FIG. 2 may be substantially altered without departing from the spirit and scope of the present invention. Any dimensions or positions known in the art that are consistent with the present invention are suitable. Several possible dimensions or positions are proposed in the patents listed and incorporated by reference above, most of which would be consistent with the present invention. Since conventional sensors use conductors with relatively low resistivity compared to conductor 240, a conventional design typically must include a very long and thin pattern to yield a sensor with a 1 ohm resistance. Conductor 240, by contrast, has a relatively high resistivity, allowing more flexibility in selecting a serpentine pattern while still yielding a sensor with a greater than 10 ohm resistance. Essentially, the higher resistivity provides a conductor 240 that need not be as thin nor as long as in conventional sensors.

Figure 3:
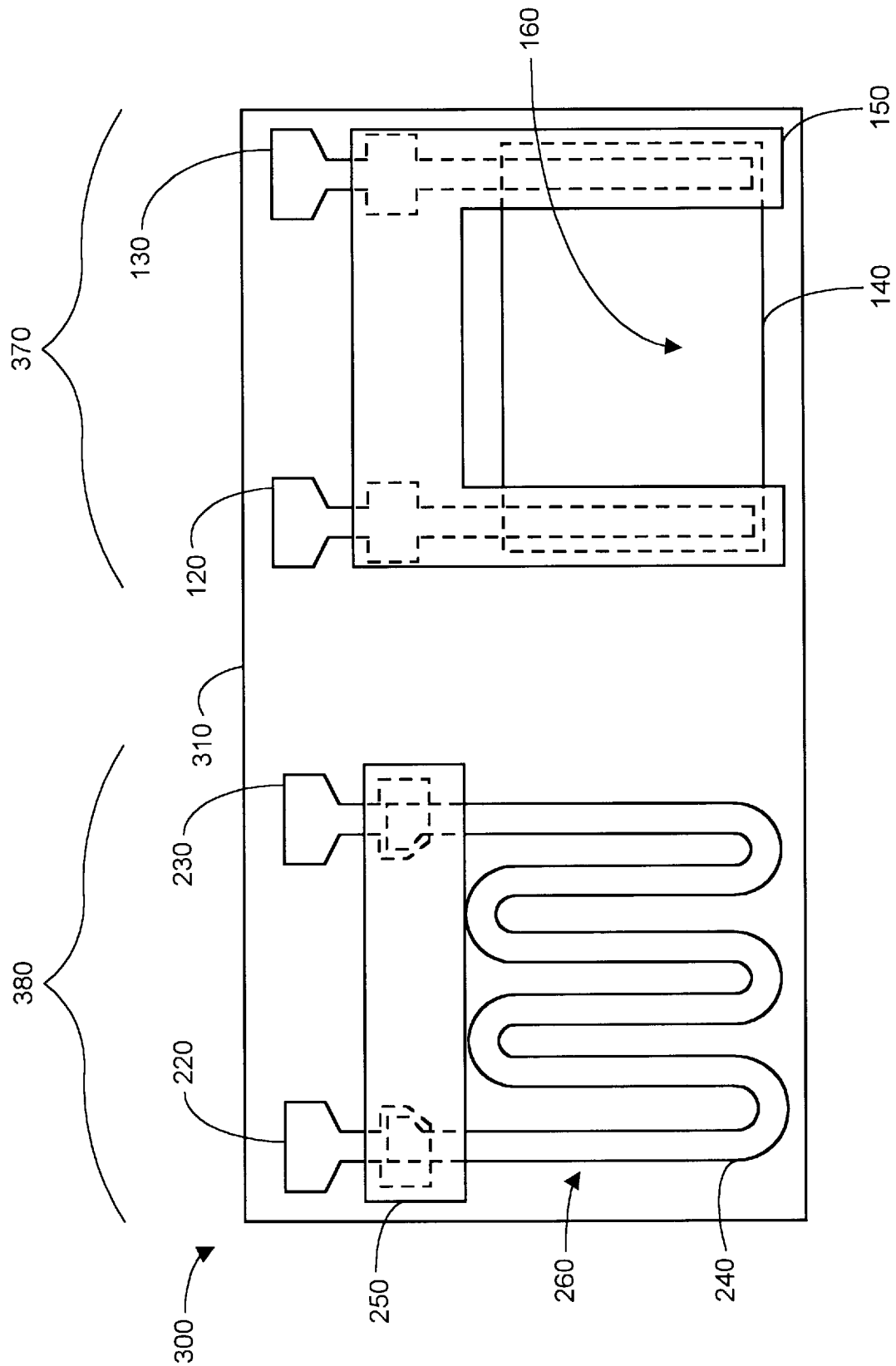
FIG. 3 is a view of a combined abrasion/corrosion sensor of the present invention.

Referring now to FIG. 3, a preferred embodiment of a combination sensor 300 is shown. The discussions above for abrasion sensor 100 and corrosion sensor 200 also apply to combination sensor 300. Combination sensor 300 includes a substrate 310, an abrasion sensor portion 370, and a corrosion sensor portion 380. Essentially, abrasion sensor portion 370 is the same as abrasion sensor 100 except that it is formed on substrate 310 along with corrosion sensor portion 380. Likewise, corrosion sensor portion 380 is the same as corrosion sensor 200 except that it is formed on substrate 310 along with abrasion sensor portion 370. One alternative embodiment to that shown in FIG. 3, is to form abrasion sensor portion 370 on one side of substrate 310 with corrosion sensor portion 380 on the other side. Abrasion sensor portion 370 is typically placed in a stream of fluid with particles impinging on sensing element 160, thus, it may be desirable to avoid possible abrasion of corrosion sensor portion 380 by forming it on an opposite side of substrate 310. If corrosion sensor portion 380 is subjected to both corrosion and abrasion, then it may give a false signal with respect to corrosiveness. This principle also holds true for corrosion sensor 200, as well as abrasion sensor portion 370 and abrasion sensor 100. That is, conductor 140 or conductor 240 should be selected and the sensors placed such that they give a true indication of abrasiveness or corrosiveness. For example, if an alloy selected for an abrasion sensor is overly susceptible to corrosion, then it may give a false indication of abrasiveness when subjected to corrosive conditions.

The principle discussed above may also be used according to the present invention to design a multi-purpose sensor (not shown). Essentially, a multi-purpose sensor incorporates attributes of both abrasion sensor 100 and corrosion sensor 200 such that it is susceptible both to abrasion and corrosion. Accordingly, a multi-purpose sensor is capable of indicating when either abrasiveness or corrosiveness exceeds a predetermined limit. In appearance, a multi-purpose sensor may resemble abrasion sensor 100, corrosion sensor 200, or some combination, keeping in mind the criteria discussed above, particularly for conductors 140 and 240. In composition, the conductor of a multi-purpose sensor is preferably a bimetallic alloy as indicated for other sensors discussed above. Such an alloy provides the high resistivity and low TCR to obviate the need for a temperature reference, etc. The primary concern in designing a multi-purpose sensor is selecting a conductor that will respond as needed to indicate both abrasiveness and corrosiveness while keeping in mind custom criteria, such as hardness and corrosion resistance as described above. As discussed above, a wide variety of alloys according to the present invention are available from which to select.

If using a multi-purpose sensor, then it will not be discernable from the sensor response alone whether it was abrasion or corrosion that caused an increase in resistance of the sensor. However, in some applications such knowledge may not be needed and a multi-purpose sensor avoids the need for having two sensors, one for abrasion and one for corrosion. For example, a multi-purpose sensor could be used in an internal combustion engine to indicate when an oil change is necessary. It may not be necessary to know why the oil needed changing since an oil change typically includes replacing both the engine oil and filter as a matter of course. Any additive-depleted oil and any faulty oil filter would be replaced regardless of whether they were the cause of the problem.

While the invention has been particularly shown and described with reference to preferred embodiments thereof, it will be understood by those skilled in the art that various changes in form and details may be made therein without departing from the spirit and scope of the invention. Accordingly, unless otherwise specified, any dimensions of the apparatus indicated in the drawings or herein are given as an example of possible dimensions and not as a limitation. Also, it will be understood that, while various of the conductors or connections are shown in the drawing as single lines, they are not so shown in a limiting sense, and may comprise plural conductors or connections, as is understood in the art.

What is desired to be claimed is:

1. A sensing element comprising:
   a) a substrate; and
   b) a conductor on the substrate, wherein the sensing element is adapted to indicate removal by abrasion or corrosion of a portion of the sensing element by an electrical resistance increase and to provide both an electrical resistance of greater than 10 ohms and a temperature coefficient of resistivity having an absolute value of less than 1000 parts per million per ° C.

2. The apparatus of claim 1, wherein the electrical resistance is greater than 100 ohms.

3. The sensor of claim 1, wherein the sensing element is formed using one of a first metal alloy including 1% to 99% palladium and a second metal alloy including 1% to 99% lead.

4. The sensor of claim 3, wherein the first metal alloy is used and wherein the first metal alloy is a bimetallic alloy including palladium and 5% to 95% gold.

5. The sensor of claim 3, wherein the second metal alloy is used and wherein the second metal alloy is a bimetallic alloy including lead and 5% to 95% metal selected from the group consisting of bismuth and palladium.

6. The sensor of claim 3, wherein the sensor is a multi-purpose sensor and wherein the first and the second metal alloys are bimetallic alloys.

7. The sensor of claim 1, wherein the sensing element comprises a thin film of a metal alloy arranged in a predetermined pattern on a substrate.

8. The sensor of claim 7, wherein:
   a) the metal alloy is a bimetallic alloy of palladium and 5% to 95% gold;
   b) a thin film of a chromium-containing substance exists between the thin film of bimetallic alloy and the substrate; and
   c) the predetermined pattern provides a target for impinging a fluid stream thereon.

9. The sensor of claim 7, wherein:
   a) the metal alloy is a bimetallic alloy of lead and 5% to 95% metal selected from the group consisting of bismuth and palladium;
   b) a thin film of a chromium-containing substance exists between the thin film of bimetallic alloy and the substrate; and
   c) the predetermined pattern comprises a serpentine shape adapted to increase sensitivity.

10. A sensor comprising a sensing element, wherein:
    a) the sensing element comprises a thin film of a metal alloy arranged in a predetermined pattern on a substrate;
    b) the metal alloy includes 1% to 99% palladium;
    c) the sensing element is adapted to indicate removal by abrasion of a portion of the sensing element by an electrical resistance increase; and
    d) the sensing element exhibits both an electrical resistance of greater than 10 ohms and a temperature coefficient of resistivity having an absolute value of less than 1000 parts per million per ° C.

11. The apparatus of claim 10, wherein the electrical resistance is greater than 100 ohms.

12. The apparatus of claim 10, wherein:
    a) the metal alloy is a bimetallic alloy of palladium and 5% to 95% gold;
    b) a thin film of a chromium-containing substance exists between the substrate and the thin film of bimetallic alloy; and
    c) the predetermined pattern provides a target for impinging a fluid stream thereon.

13. A sensor comprising a sensing element, wherein:
    a) the sensing element comprises a thin film of a metal alloy arranged in a predetermined pattern on a substrate;
    b) the metal alloy includes 1% to 99% lead;
    c) the sensing element is adapted to indicate removal by corrosion of a portion of the sensing element by an electrical resistance increase; and
    d) the sensing element exhibits both an electrical resistance of greater than 10 ohms and a temperature coefficient of resistivity having, an absolute value of less than 1000 parts per million per ° C.

14. The apparatus of claim 13, wherein the electrical resistance is greater than 100 ohms.

15. The apparatus of claim 7, wherein:
    a) the metal alloy is a bimetallic alloy of lead and 5% to 95% metal selected from the group consisting of bismuth and palladium;
    b) a thin film of a chromium-containing substance exists between the substrate and the thin film of bimetallic alloy; and
    c) the predetermined pattern comprises a serpentine shape adapted to increase sensitivity.

16. An apparatus comprising a combination sensor having:
    a first conductive sensing element, wherein a first voltage applied across the first sensing element creates a first sensing current used to determine a first electrical resistance, wherein the first sensing element has dimensions and a composition adapted to indicate removal by abrasion of a portion of the first sensing element by a first increase in the first electrical resistance and to provide a first resistance large enough that predetermined magnitudes of noise voltage do not influence the first sensing current to create a false indication of removal, and wherein the first sensing element composition is also adapted to provide a first temperature coefficient of resistivity small enough that measurement of the first increase in resistance is substantially independent of temperature; and a second conductive sensing element, wherein a second voltage applied across the second sensing element creates a second sensing current used to determine a second electrical resistance, wherein the second sensing element has dimensions and a composition adapted to indicate removal by corrosion of a portion of the second sensing element by a second increase in the second electrical resistance and to provide a second resistance large enough that predetermined magnitudes of noise voltage do not influence the second sensing current to create a false indication of removal, and wherein the second sensing element composition is also adapted to provide a second temperature coefficient of resistivity small enough that measurement of the second increase in resistance is substantially independent of temperature.

17. The apparatus of claim 16, wherein the first and second electrical resistance are greater than 10 ohms and the first and second temperature coefficients of resistivity have an absolute value of less than 1000 parts per million per ° C.

18. The apparatus of claim 16, wherein:
a) the first sensing element includes a thin film of a first metal alloy arranged in a first predetermined pattern on a substrate;
b) the first metal alloy comprises 1% to 99% palladium;
c) the second sensing element includes a thin film of a second metal alloy arranged in a second predetermined pattern on a substrate; and
d) the second metal alloy comprises 1% to 99% lead.

19. The apparatus of claim 18, wherein:
a) the first metal alloy is a first bimetallic alloy of palladium and 5% to 95% gold;
b) a first thin film of a chromium-containing substance exists between the substrate and the thin film of the first bimetallic alloy;
c) the first predetermined pattern comprises a target for impinging a fluid stream thereon;
d) the second metal alloy is a second bimetallic alloy of lead and 5% to 95% metal selected from the group consisting of bismuth and palladium;
e) a second thin film of a chromium-containing substance exists between the substrate and the thin film of the second bimetallic alloy; and
f) the second predetermined pattern comprises a serpentine shape adapted to increase sensitivity.

20. A combination sensor comprising:
a) a first sensing element including a first conductor on a substrate, wherein the first sensing element is adapted to indicate removal by abrasion of a portion of the first sensing element by a first electrical resistance increase; and
b) a second sensing element including a second conductor on the substrate, wherein the second sensing element is adapted to indicate removal by corrosion of a portion of the second sensing element by a second electrical resistance increase.

21. The sensor of claim 20, wherein:
a) the first sensing element further exhibits both a first electrical resistance large enough for the first resistance increase to be substantially independent of noise voltage and a first temperature coefficient of resistivity small enough for the first resistance increase to be substantially independent of temperature; and
b) the second sensing element further exhibits both a second electrical resistance large enough for the second resistance increase to be substantially independent of noise voltage and a second temperature coefficient of resistivity small enough for the second resistance increase to be substantially independent of temperature.

22. The sensor of claim 21, wherein the first and second electrical resistance are greater than 10 ohms and the first and second temperature coefficients of resistivity have an absolute value of less than 1000 parts per million per C.

23. The sensor of claim 20 wherein:
a) the first sensing element includes a thin film of a first metal alloy arranged in a first predetermined pattern on a substrate;
b) the first metal alloy comprises 1% to 99% palladium;
c) the second sensing element includes a thin film of a second metal alloy arranged in a second predetermined pattern on a substrate; and
d) the second metal alloy comprises 1% to 99% lead.

24. The apparatus of claim 23, wherein:
a) the first metal alloy is a first bimetallic alloy of palladium and 5% to 95% gold;
b) a first thin film of a chromium-containing substance exists between the substrate and the thin film of the first bimetallic alloy;
c) the first predetermined pattern comprises a target for impinging a fluid stream thereon;
d) the second metal alloy is a second bimetallic alloy of lead and 5% to 95% metal selected from the group consisting of bismuth and palladium;
e) a second thin film of a chromium-containing substance exists between the substrate and the thin film of the second bimetallic alloy; and
f) the second predetermined pattern comprises a serpentine shape adapted to increase sensitivity.

* * * * *